United States Patent [19]

Takada et al.

[11] 4,203,906

[45] May 20, 1980

[54] PROCESS FOR CATALYTIC VAPOR PHASE OXIDATION

[75] Inventors: Masahiro Takada; Hiroyuki Uhara, both of Tatsuno; Takahisa Sato, Himeji, all of Japan

[73] Assignee: Nippon Shokubai Kagaku Kogyo Co., Ltd., Osaka, Japan

[21] Appl. No.: 922,791

[22] Filed: Jul. 7, 1978

[30] Foreign Application Priority Data

Jul. 13, 1977 [JP] Japan .................................. 52-83036
Jul. 14, 1977 [JP] Japan .................................. 52-83609
Jul. 20, 1977 [JP] Japan .................................. 52-86010

[51] Int. Cl.$^2$ ......................................... C07D 307/89
[52] U.S. Cl. .................................. 260/346.4; 260/385; 260/396 R; 260/346.75; 260/465 C; 260/465.3; 260/687 R; 562/545; 562/546; 562/547; 422/201; 568/479; 568/480; 568/476
[58] Field of Search ............... 260/385, 396 R, 346.4, 260/346.75, 465 C, 465.3, 604 R; 562/545–547

[56] References Cited

U.S. PATENT DOCUMENTS 3,129,230 4/1964 Hughes ........................... 260/346.4
3,180,877 4/1965 Benichou et al. ................. 260/346.4
3,353,923 11/1967 Pelers ........................... 260/346.4 X

*Primary Examiner*—Richard Raymond
*Attorney, Agent, or Firm*—Omri M. Behr

[57] ABSTRACT

A process for catalytic vapor phase oxidation which comprises using a fixed-bed shell and tube heat exchange type reactor in which a bundle of a multiplicity of tubes filled with at least one type of oxidizing catalyst are disposed in a shell and these tubes are passed through the apertures formed in at least one perforated shield plate to partition the inside of the shell into at least two heat transfer medium feed zones and in such a manner that each of the tubes passing through the perforated shield plate is not in direct contaction with the shield plate but the outer surface of the tube and the inner surface of the aperture are spaced apart by a distance of between 0.2–5 mm, supplying feed gas to the tubes of the reactor, and conducting exothermic catalytic vapor phase oxidation while controlling the temperatures for the heat transfer medium in each of the zones so that the temperature difference between each of the zones can be maintained between 0°–100° C.

13 Claims, 5 Drawing Figures

PROCESS FOR CATALYTIC VAPOR PHASE OXIDATION

This invention relates to a process for catalytic vapor phase oxidation and a reactor used therefor and, in particular, to a process for catalytically oxidizing hydrocarbons in vapor phase using a fixed bed multi-tubular heat exchange type reactor. More specifically, it concerns a structure of a multi-tubular heat exchange type reactor which can keep a catalyst used therein at optimum reaction conditions and restrict the generation of hot spots (abnormal local heating in catalyst layers), upon exothermic catalytic vapor phase oxidation of hydrocarbons, and a method of using such a reactor.

Catalytic vapor phase oxidations are generally highly exothermic and it is thus very important to control the reaction temperature within a certain range and restrict the generation of hot spots in the reaction zones, which imposes great efforts on those skilled in the art. No satisfactory control of the catalytic reaction temperature with the catalysts can be attained only with the uniform circulation of heat transfer medium in a reactor and hot spots appear frequently to result in excess oxidation locally in the reactor, particularly where the oxidation reaction has to be proceeded sequentially to convert starting materials into end products such as in the oxidation of naphthalene or o-xylene into phthalic anhydride, oxidation of benzene, butylene or butadiene into maleic anhydride, oxidation of propylene into acrolein or acrylic acid, oxidation of ethylene into ethylene oxide, ammoxidation of propylene into acrylonitrile, ammoxidation of aromatic hydrocarbons such as toluene and xylene into aromatic nitriles such as benzonitrile, phthalonitrile and the like. As the result undesired combustion reaction is increased to lower the yield of the aimed products. In addition, since the catalysts are always exposed locally to high temperature by the presence of the hot spots, the life of the catalysts is decreased in that portion to result in disadvantages.

Various counter measures have been employed in order to overcome the foregoing disadvantages in the vapor phase oxidation. As one of the most popular methods, the diameter of catalyst filled tube is decreased in order to increase the heat transfer rate per unit volume of the catalyst. This method is, however, defective in that the number of the filled tube is increased and it increases the fabrication cost of the reactor, as well as takes much time for the charging and discharging of the catalyst.

In other effective methods proposed so far, catalyst layer is diluted with an inert substance or, as disclosed in Japanese Published Unexamined Patent Application No. 85485/1973, generation of hot spots is restricted by the insertion of cylindrical material containing closed cavity in the center at the cross section of a reaction tube filled with the catalyst entirely or partially in the axial direction of it thereby providing a space in which no catalyst is present and no reaction mixture passes through. This method is, however, defective in that the cost is inevitably increased by so much as the substantially inert material is contained. It has a further defect that recovery of useful metal components from the catalyst removed from the reactor after the degradation of the catalytic activity is very laborious to lower the recovery efficiency.

A further effective method suppresses the temperature rise in the hot spots by gradually increasing the activity of the catalyst from the inlet to the outlet in the reaction tube. This method, however, requires at least two types of catalysts of different catalytic activities, and no optimum reaction temperatures can be selected for respective catalysts charged in each of the layers. Moreover, if these catalysts show different degrees of aging changes in their catalytic activities, control and keeping of the optimum reaction temperatures are further difficult to inevitably lower the over all yield for the desired products.

A still further effective method is proposed as disclosed in U.S. Pat. No. 3,147,084 and in German Laid Open Patent Publication No. 2,513,405 wherein a shell of a multi-tubular heat exchange type reactor is entirely partitioned with a shield plate into two heat transfer medium feed zones and reaction is carried out while circulating heat transfer medium at different temperatures in each of the zones. It is, however, very difficult to this method to insert as many as several thousands of reaction tubes into a perforated plate used as the shield plate in the reactor, and those portions between the perforated plate and the reaction tubes that are contacted by the heat expansion of the tubes are abrased by the pulsation of the heat transfer medium to cause corrosion and destruction unless the reaction tubes and the perforated plate are secured to each other by welding or expanding the diameter of the reaction tubes. The above securing fabrication however requires troublesome works such as accurate perforation, welding and diameter expansion over several thousands of portions.

It is, accordingly, an object of this invention to provide an improved process of catalytic vapor phase oxidation and a reactor used therefor.

It is another object of this invention to provide a process of catalytic vapor phase oxidation in which catalyst is kept at its optimum reaction conditions and an apparatus used therefor.

It is a further object of this invention to provide a structure of a multi-tubular heat exchange type reactor capable of restricting the generation of hot spots and a method of using such a reactor.

These objects of this invention can be attained by the catalytic vapor phase oxidation process which comprises using a fixed-bed shell and tube heat exchange type reactor in which a bundle of multiplicity of tubes filled with at least one type of oxidation catalyst is disposed in a shell and these tubes are passed through the apertures perforation in at least one perforated shield plate to partition the shell into at least two heat transfer medium feed zones in such a way that each of the tubes passed through the perforated sheild plate is not in direct contaction with the shield plate but the outer surface of the tubes and the inner surface of the apertures are spaced apart with a distance between 0.2–5 mm, feeding feed gas to the tubes of the reactor, and conducting the exothermic catalytic vapor phase oxidation while controlling the temperatures of the heat transfer medium in each of the zones partitioned by the shield plate so that the temperature difference therebetween is kept within the range between 0°–100° C.

In order to obtain high yield an improved reactor for varying reaction temperatures corresponding to reaction stages has hitherto been proposed (Japanese Published Unexamined Patent Application No. 80473/1973.) However, settlement of the temperature described in the Patent Application No. 80473/1973 is to carry out the reaction smoothly by providing a controller in a circulation mechanism of the heat transfer medium, so it is difficult to obtain almost shielded reaction temperature zones as in the present invention. In the above process it is rather proposed to provide reaction zones wherein the heat transfer mediums are completely separated each other as a means for obtaining such shielded reaction temperature zones. Therefore, it is clear that the present invention relates to a simple and economical reactor having a novel constitution in stead of a conventional case.

The reactor specified as foregoings in the process of the present invention has an advantage in that the structure is simple to make the fabrication process simplified and reduce the fabrication cost and, in addition, it has a further feature as detailed hereinafter, that no substantial heat distortion is generated. The use of this reactor in catalytic vapor phase oxidation enables to control the temperature of the heat transfer medium in the catalyst layer region where exotherm is most significant to a lower level than the temperature for the heat transfer medium in other region to restrict the exotherm in the hot spots. This enables to increase the conversion rate of the feed gas to be oxidized in the succeeding zone substantially to 100% and thus permits most effective utilization of the catalyst. Particularly, the use of the above reactor according to this invention in the catalytic vapor phase reaction where the reaction is proceeded sequentially, restricts useless combustion caused by the over oxidation in the hot spots to ensure improved yield in the desired products and enables to increase the concentration of the starting material as compared with that in the conventional catalytic vapor phase reaction. The reaction where catalysts and reaction temperatures are different in each of the reaction steps and, hence, two or more reactors have been required so far can be conducted with only one reactor by the process according to this invention. Moreover, this invention provides a further merit that the catalyst life is prolonged astonishingly.

This invention will be understood best in connection with the accompanying drawings, wherein.

Figure 1:
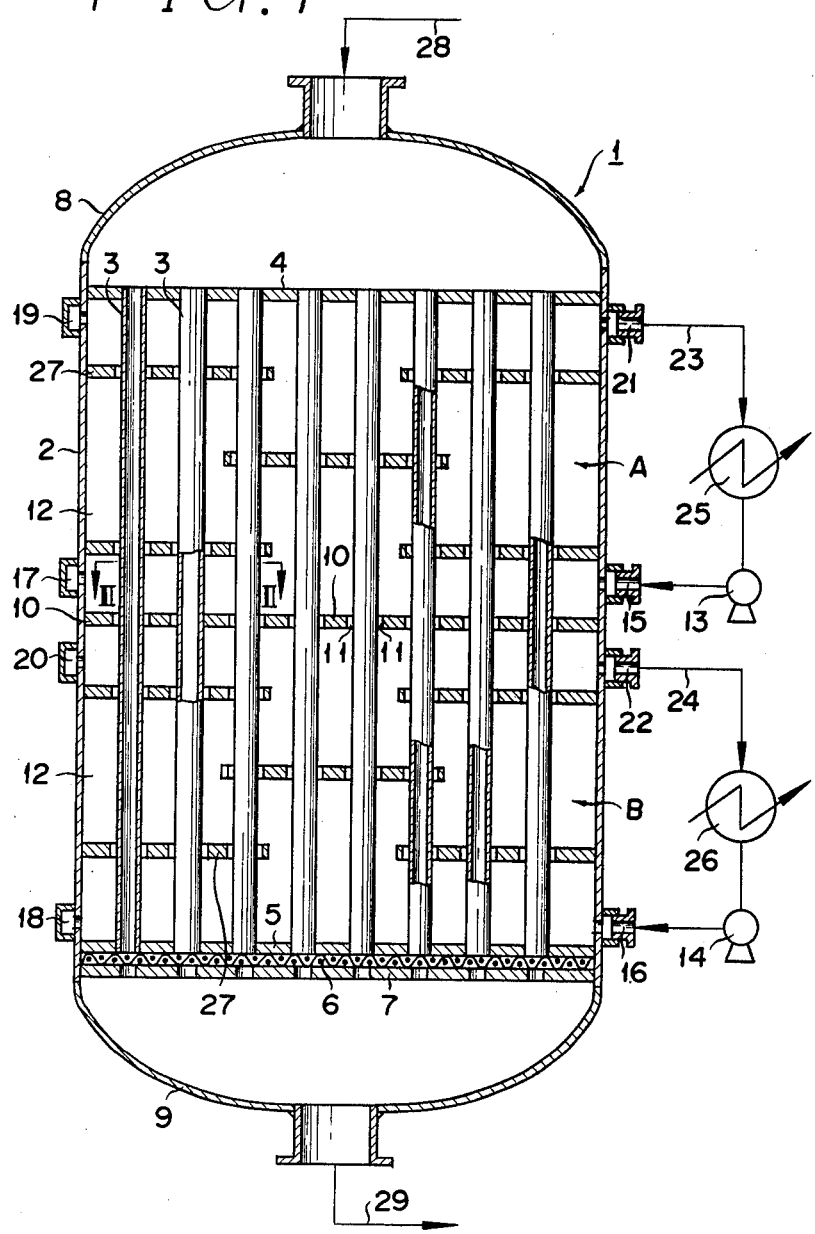
FIG. 1 is a vertical cross sectional view of a reactor for carrying out the process of this invention.
Figure 2:
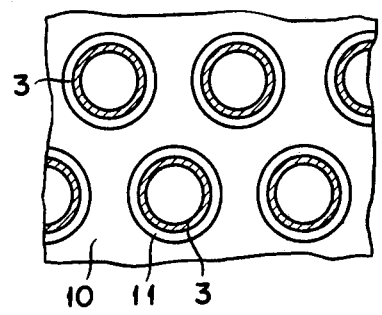
FIG. 2 is a cross sectional view of a part taken along line II—II in FIG. 1.

FIG. 1 shows one example of a fixed-bed type shell and tube heat exchange type reactor 1, whose shell 2 contains in its inside a lot of (for example several hundreds to several thousands or more) reaction tubes in a diameter, for example, of 5–50 mm loaded in parallel with the axis of the shell 2. Each of the reaction tubes 3 is fitted at its upper and the lower end respectively to each of the apertures in tube plates 4 and 5 respectively and secured thereto by means of diameter expansion and welding. At the lower portion of the reaction tubes, are secured a wire mesh screen 6 for the prevention of catalyst falling and a perforated plate 7 to the shell 2 by means of welding and the like. The shell 2 is secured at its upper and the lower ends with a front cap 8 and a rear cap 9 by means of welding or the like. The inside of the shell 2 is divided into at least two heat transfer medium zones A and B by the disposition of at least one perforated plate 10 at a desired position, to the apertures 11 of which are passed through the reaction tubes 3. As shown in FIG. 1 and FIG. 2, the perforated shield plate 10 is not in direct contaction with each of the reaction tubes 3 passing therethrough but the outer surface of the reaction tube 3 and the inner surface of the apertures 11 are spaced apart at a distance between 0.2–5 mm. The presence of the distance is important. If the reaction tubes 3 and the shield plate 10 are arranged closed or secured to each other with no gaps, the reaction tubes 3 and the shield plate 10 are undesirably contacted to each other and abrased due to the heat distortion resulted in the reaction tubes 3 or the shield plate 10 because of the temperature difference between the zones A and B, or frequent heating or cooling effected in the reactor. Moreover, the fabrication of the reactor is laborious and costly. On the contrary, too wide gap makes the temperature control more difficult as the amount of heat medium moving between the zones A and B is increased. It is required, based on our experience, that the distance between the outer surface of the reaction tube 3 and the inner surface of the apertures 11 in the shield plate 10 is between 0.2–5 mm and, preferably, 0.3–1 mm for performing satisfactory temperature control with no substantial movement of the heat transfer medium between the zones A and B.

Heat transfer medium for heat exchange is supplied to the outer side 12 of the reaction tube bundle (shell side) in the reactor 1 for keeping the reaction temperature constant in the reaction tubes and it is introduced for heat exchange by way of a volute pump or an axial flow pump 13 and 14 from inlets 15 and 16 and through annular conduits 17 and 18 into the zones A and B respectively. Then, it is discharged through annular conduits 19 and 20 and from exits 21 and 22 respectively and sent to heat exchangers (or heating devices) 25 and 26 for cooling (or heating) and then further circulated.

The method of circulating the heat transfer medium is noway limited only to the foregoing method. If the temperature difference is very great between the zones A and B, keeping and control of the reaction temperature can be facilitated by making lateral flow directions of the heat transfer medium at the shield plate 10 identical by introducing the heat medium from the outlet 22 in the zone B where the heat medium is introduced from the inlet 15 in the zone A. It is also possible to provide a flow control mechanism to each of the circulating mechanisms for facilitating the temperature control in each of the temperature zones, and either one of the heat transfer medium cooling (or heating) means 25 and 26 can be saved where exotherm (or endotherm) in the zones A and B, the moving amount of the heat transfer medium between the zones A and B and the circulating amount of the heat transfer medium by way of the circulating devices of the pumps 13 and 14 are known previously.

Number of the shield plates 10 may be increased to more than one where more strict temperature control is required for both of the zones A and B. It is recommended, where the reactor has a great diameter and thus a lot of reaction tubes, to change the direction of flow direction of the heat transfer medium by buffle plates 27 to thereby increase the heat exchange efficiency.

At least one type of catalyst in the form of granule such as in spherical, pellet and irregular form is charged in the reaction tube 3 and the feed gas is supplied through the conduit 28 to the reactor 1 and the gas contacts the catalyst in the reaction tube 3 to conduct the oxidation reaction. The reaction heat generated in the course of the reaction is heat exchanged with the heat transfer medium to keep the catalyst layer at a predetermined temperature. The reaction mixture containing the desired products is sent through the conduit 29 to collection, recovery and purification steps. In the above reaction steps, the starting reaction material may be adversely introduced from the conduit 29, passed through the reaction tube 3 and then discharged out of the conduit 28.

Figure 3:
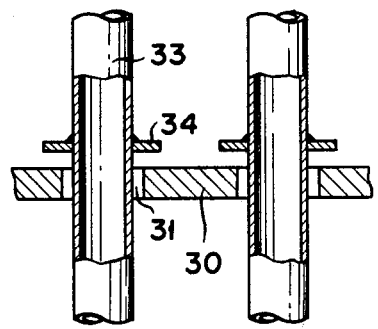
FIG. 3 is a cross sectional view of a part of the shield plate mounting portion in another embodiment of this invention.

FIG. 3 shows another embodiment of this invention and it shows a vertical section of a part of a shield plate 30 in which no substantial movement of the heat transfer medium is taken place between the zones A and B by annular fins 34 secured to reaction tubes 33. It is so device that the heat transfer medium can be moved by keeping the distance between the outer surface of the reaction tube 33 and the inner surface of the apertures 31 in the shield plate 30 to between 0.2-5 mm. The presence of the distance is important and, if the reaction tube 33 and the shield plate 30 are closed too nearly or secured to each other, the reaction tube and the shield plate are undesirably contacted and abrased where temperature difference between the zones A and B is great or frequent heating or cooling is taken place in the reactor. Moreover, fabrication of the reactor is laborious. On the contrary, it is not necessary and disadvantageous to make the gap excessively wide. Since the distance between the reaction tube and another is selected between 6-30 mm in a usual multi-tubular reactor, the distance between the shield plate and the reaction tube is naturally restricted thereby.

The fin is secured to the reaction tube in such a manner as it covers the distance described above as shown in FIG. 3. The distance between the fin and the shield plate is controlled to between 0.2-5 mm and, preferably, 0.3-1 mm, whereby no substantial movement of the heat transfer medium between zones A and B is effected in its circulation and the temperature for each of the reaction temperature zones can be controlled with satisfaction.

Figure 4:
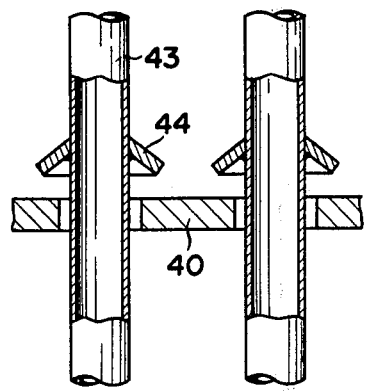
FIG. 4 is a cross sectional view of a part of the shield plate mounting portion in still another embodiment of this invention.
Figure 5:
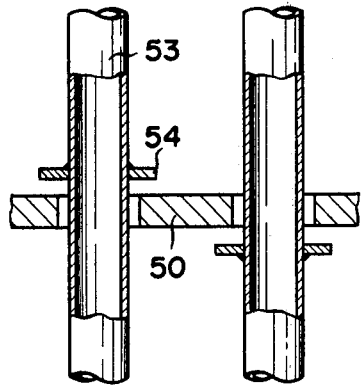
FIG. 5 is a cross sectional view of a part of the shield plate mounting portion in a still further embodiment of this invention.

The fin may be disposed in parallel with the shield plate or it may be secured to the reaction tube 43 in such a manner that the top end of the fin 44 comes nearest to the shield plate as shown in FIG. 4. The fin 44 may be attached either above or below the shield plate 40, or as shown in FIG. 5 fins 54 may be attached to a shield plate 53 so that they alternately comes above and below the shield plate 50.

The distance above described as between 0.2-5 mm, preferably, 0.3-1 mm is somewhat influenced by the type of the heat transfer medium used. When highly viscous medium, for example, molten salt (mainly composed of a mixture of potassium nitrate and sodium nitrite) is used, the reaction temperature is high and the amount of the heat transfer medium passing through the gap can be small even if the distance is somewhat wide. In using other heat transfer medium such as phenyl ether medium (for example "Dowtherm") and polyphenyl medium (for example "Therm S"), it is, however, desired to make the distance somewhat narrower even in a lower temperature reaction as compared with the use of the molten salts.

The heat transfer medium used in this invention include, in addition to the above medium, hot oil, naphthalene derivatives (S.K. oil), mercury and the like.

While the process of this invention can be applied to any exothermic catalytic vapor phase oxidation, it is particularly advantageous for the catalytic vapor phase oxidation of hydrocarbons including various production processes such as oxidation of naphthalene or o-xylene into phthalic anhydride, oxidation of benzene, butylene or butadiene into maleic anhydride oxidation of propylene into acrolein or acrylic acid, oxidation of ethylene into ethylene oxide, ammoxidation of propylene into acrylonitrile, oxidation of isobutylene into methacrolein or methacrylic acid, ammoxidation of isobutylene into methacrylonitrile, ammoxidation of aromatic hydrocarbons such as toluene and xylene into aromatic nitriles such as benzonitrile and phthalonitrile, oxidation of naphthalene into naphthoquinone, and oxidation of anthracene into anthraquinone. In these reactions, hydrocarbons and molecular oxygen are introduced at the co-existence of an inert gas if required into the reactor and oxidized into a desired product.

The catalytic vapor phase oxidation can thus be effected with an extreme ease by using the reactor specified in this invention. As stated above, while the reactor defined by the present invention is best suited to the conduction of the sequential oxidation, it has been found based on our experience that the temperature difference as great as 100° C. at the maximum can be set between the heat transfer medium in each of the zones. The temperature difference between the heat transfer medium in each of the zones is therefore between 0°-100° C. and, preferably, 0°-80° C. As for the reason of necessity of the temperature difference of 0° C. specified in above, there is a case that two or more sequential reactions having highly different heats of reaction from each other can be advantageously carried out at nearly the same temperature only by controlling the flow rates of the heat transfer medium in each zone in the reactor of this invention. Further, it means that at the beginning of the reaction, even if several tens degree centigrade of temperature difference is required, activities of the catalyst varies gradually with the lapse of time and the temperature difference between each zone decreases, and finally the temperature difference is sometimes reversed.

More specifically, in the production of phthalic anhydride from o-xylene or naphthalene using two reaction temperature zones A and B, temperature between 300°-400° C. is employed in the preceeding stage and the temperature between 350°-450° C. is employed in the subsequent stage and the temperature difference has to be kept between 30°-60° C. if the catalyst of a same composition is employed. Such a condition can be satisfied with ease. In the oxidation of benzene, butylene or butadiene into maleic anhydride using two reaction temperature zones A and B, the temperature for the preceeding stage is at 320°-400° C. and the temperature for the subsequent stage is at 350°-450° C. and it is required to maintain the temperature difference between 20°-50° C. The above condition can also be satisfied with ease.

Satisfactory results can also be obtained in carrying out the process of this invention using catalysts of two or more different compositions, because the reaction can be proceeded at reaction temperatures more suited to the performance of the respective catalysts.

It has been found, more characteristically to this invention, that the process according to this invention is also applicable to such catalytic upon phase oxidation as comprising a preceeding oxidation of propylene into acrolein and a suceeding oxidation of the acrolein into acrylic acid where the reaction temperature in each of the reaction zones is different as much as by 50°–100° C.

EXAMPLE 1

O-xylene was catalytically oxidized by air in vapor phase into phthalic anhydride using a vertical type multi-tubular reactor as shown in FIG. 1 having 24 steel tubes 4 m in length, 25.0 mm in inside diameter and 29.0 mm in outside diameter, in which a shield plate is situated at the half height of the reactor and the distance between the reaction tubes passing through the shield plate and the shield plate was adjusted to about 0.6 mm. The catalyst employed in this oxidation reaction was prepared in accordance with the description of Example 1 in U.S. Pat. No. 3,926,846 and had a catalyst composition: $V_2O_5:TiO_2=2.1:97.9$ on the weight basis and, based on the total weight of $V_2O_5$ and $TiO_2$, 0.49% by weight of $P_2O_5$, 0.146% by weight of $K_2O$ and 0.25% by weight of $Nb_2O_5$. The porosity of the catalyst was measured by mercury porosimeter, and the pore volume of pore diameters of 0.10–0.45 micron amounted to 86% of the total volume of pores of diameters of less than 10 microns.

The catalyst thus prepared was charged by 1,500 cc per one reaction tube so as to give a 3 m catalyst layer length, 1 m of the total layer length situating a temperature zone in the preceeding Stage (A) and remaining 2 m situating in the temperature zone in the subsequent stage (B).

In the initial stage of the reaction, the temperature of the molten salt on the shell side of the reactor was maintained at 355° C. in the temperature zone A and at 375° C. in the temperature zone B, and the reaction was started at a concentration of 20 (l) air/o-xylene (g) and at a space velocity (S.V.) of 4,000 $hr^{-1}$. The reaction was continued thereafter for one year while controlling the temperature in both of the temperature zones A and B so that the optimum yield was obtained for phthalic anhydride. The result are shown in Table 1. In the Table 1, the yield for phthalic anhydride is expressed by weight % based on o-xylene supplied. The gas concentration (G.C.) is for the concentration air (l)/o-xylene (g).

Table 1

| Time elapsed | Reaction temperature (°C.) A | B | S.V. ($hr^{-1}$) | G.C. (l/g) | Phthalic anhydride yield (wt. %) |
|---|---|---|---|---|---|
| Initial | 355 | 375 | 4,000 | 20 | 115.3 |
| 3 month | 355 | 375 | 4,000 | 20 | 115.0 |
| 6 month | 357 | 375 | 4,000 | 20 | 114.5 |
| 12 month | 359 | 375 | 4,000 | 20 | 114.1 |

COMPARATIVE EXAMPLE 1

Reaction was continued for 12 months while using the same catalyst as in Example 1, using a same scale of a reactor as in Example 1 where no shield plate is provided so as to form a single temperature zone and under the reaction conditions shown in Table 2. The results are also shown in Table 2.

Table 2

| Time elapsed | Reaction temperature (°C.) | S.V. ($hr^{-1}$) | G.C. (l/g) | Phthalic anhydride yield (wt.%) |
|---|---|---|---|---|
| Initial | 370 | 4,000 | 20 | 112.8 |
| 3 month | 375 | 4,000 | 20 | 112.1 |
| 6 month | 381 | 4,000 | 20 | 110.4 |
| 12 month | 390 | 4,000 | 20 | 105.9 |

EXAMPLE 2

Reaction was conducted for 12 months using the same catalyst and the same reactor as those in Example 1, increasing the gas concentration to 16 (l) air/o-xylene (g) and under the reaction conditions as shown in Table 3. The results are shown in Table 3.

Table 3

| Time elapsed | Reaction temperature (°C.) A | B | S.V. ($hr^{-1}$) | G.C. (l/g) | Phthalic anhydride yield (wt. %) |
|---|---|---|---|---|---|
| Initial | 360 | 380 | 4,000 | 16 | 114.5 |
| 3 month | 363 | 380 | 4,000 | 16 | 113.9 |
| 6 month | 365 | 383 | 4,000 | 16 | 113.5 |
| 12 month | 368 | 389 | 4,000 | 16 | 113.0 |

COMPARATIVE EXAMPLE 2

Reaction was continued for 3 months increasing the gas concentration in Comparative Example 1 to 16 (l) air/o-xylene (g) and under the reaction conditions shown in Table 4. The results are shown in Table 4.

Table 4

| Time elapsed | Reaction temperature (°C.) | S.V. ($hr^{-1}$) | G.C. (l/g) | Phthalic anhydride yield (wt. %) |
|---|---|---|---|---|
| Initial | 380 | 4,000 | 16 | 104.1 |
| 3 month | 407 | 4,000 | 16 | 97.7 |

EXAMPLE 3

Phthalic anhydride was prepared according to the process in Example 1 and using two types of catalysts. The catalysts were prepared according to the descriptions of Example 1 in U.S. Pat. No. 4,046,780. A catalyst having a catalytically active substance of a composition: $V_2O_5:TiO_2:Nb_2O_5:P_2O_5:K_2O:Na_2O = 2:98:0.25:1.02:0.15:0.1$ (weight base) was prepared as the catalyst for the preceeding stage. The porosity distribution of the catalyst was measured by a mercury porosimeter. The pore volume of pore diameters of 0.15–0.45 micron amounted to 88% of the total pore volume of pores of diameters of less than 10 microns, which is to be referred to as 88% pore volume of 0.15–0.45 micron hereinafter. The catalyst was used as the preceeding stage catalyst.

Then, another catalyst having a catalytically active substance of a composition: $V_2O_5:TiO_2:Nb_2O_5:P_2O_5:K_2O:Na_2O = 2:98:0.25:1.3:0.15:0.1$ (weight basis) and having 87% pore volume of 0.15–0.45 micron was prepared as the subsequent stage catalyst.

The catalysts thus prepared were charged in the reaction tubes in the same reactor as employed in Example 1 in which the subsequent stage catalyst was filled to a length of 1.5 m in the temperature zone B and then the preceedding zone catalyst was filled to a length of 1.5 m in the temperature zone A and the reaction was effected. The reaction conditions and the results of the reaction are shown in Table 5.

Table 5

| Time elapsed | Reaction temperature (°C.) A | B | S.V. (hr$^{-1}$) | G.C. (l/g) | Phthalic anhydride yield (wt. %) |
|---|---|---|---|---|---|
| Initial | 360 | 375 | 3,500 | 16.6 | 117.2 |
| 3 month | 365 | 375 | 3,500 | 16.6 | 117.0 |
| 6 month | 370 | 375 | 3,500 | 16.6 | 116.9 |

EXAMPLE 4

Maleic anhydride was obtained from benzene in the same reactor as in Example 1. The catalyst used in this oxidation was prepared according to the descriptions of Example 1 in U.S. Pat. No. 4,036,780. The completed catalyst prepared had a catalytically active substances of a composition: $V_2O_5:MoO_3:P_2O_5:Na_2O = 1:0.40:0.015:0.06$ (molar ratio).

The catalyst thus prepared was charged by 1,500 cc per one reaction tube so as to give a 3 m catalyst layer length.

In the initial stage of the reaction, temperature was maintained at 345° C. for the temperature zone A and at 370° C. for the temperature zone B, and the reaction was started at a gas concentration of 22 (l) air/benzene (g) and at a space velocity of 2500 hr$^{-1}$ (NTP). The reaction was continued thereafter for 12 months while controlling the temperatures for both of the zones A and B so that the best yield was obtained for the yield of maleic anhydride. The results are shown in Table 6.

Table 6

| Time elapsed | Reaction temperature (°C.) A | B | S.V. (hr$^{-1}$) | G.C. (l/g) | Maleic anhydride Yield (wt. %) |
|---|---|---|---|---|---|
| Initial | 345 | 370 | 2,500 | 22 | 94.2 |
| 3 month | 347 | 370 | 2,500 | 22 | 92.8 |
| 6 month | 350 | 372 | 2,500 | 22 | 93.0 |
| 12 month | 355 | 375 | 2,500 | 22 | 92.7 |

COMPARATIVE EXAMPLE 3

Reaction was continued using the same catalyst as employed in Example 4 and employing a same scale of a reactor as used in Example 4, in which no shield plate was provided so as to form a single temperature zone and under the reaction conditions shown in Table 7. The results are shown in Table 7.

Table 7

| Time elapsed | Reaction temperature (°C.) | S.V. (hr$^{-1}$) | G.C. (l/g) | Maleic anhydride yield (wt. %) |
|---|---|---|---|---|
| Initial | 370 | 2,500 | 22 | 93.2 |
| 3 month | 378 | 2,500 | 22 | 90.0 |
| 6 month | 385 | 2,500 | 22 | 85.3 |
| 12 month | 390 | 2,500 | 22 | 81.7 |

EXAMPLE 5

Acrylic acid was obtained by the oxidation of propylene in a similar reactor to that in Example 1 excepting that the length of a reaction tube was 6 m. As the catalysts used in this oxidation, a preceeding stage catalyst for mainly preparing acrolein from propylene was prepared according to the descriptions of Example 1 in U.S. Pat. No. 3,825,600 and the subsequent stage catalyst for oxidizing the acrolein into acrylic acid was prepared according to the descriptions of Example 1 in U.S. Pat. No. 3,833,649. The preceeding stage catalyst was an oxidizing catalyst having a composition, except for oxygen, of: $Co_4Fe_1Bi_1W_2Mo_{10}Si_{1.35}K_{0.06}$ in atomic ratio, and the subsequent stage catalyst was an oxidizing catalyst supported on a support and having a metal composition of: $Mo_{12}V_{4.6}Cu_{2.2}Cr_{0.6}W_{2.4}$.

The subsequent stage catalyst was at first charged each by 1,250 cc per one reaction tube in the temperature zone B to form a layer height of 2.5 m. Then, 250 cc of 5 mm of diameter of spheric alundum was filled thereover for cooling reaction gas in such a manner that its upper end levelled with the plane of the shield plate. Then, the preceeding stage catalyst was charged further thereover so as to form a 2.4 m charged layer length. A gas mixture having a reaction gas composition of 7.0% by volume of propylene, 12.6% by volume of oxygen, 10.0% by volume of steam and balance of inert gas mainly containing nitrogen was supplied to the preceeding stage catalyst at a space velocity (S.V.) of 1,350 hr$^{-1}$ (NTP) and the reaction was started while maintaining the temperature of 320° C. for the temperature zone A and at 255° C. for the temperature zone B at the initial stage of the reaction. The reaction was continued thereafter for 12 months while controlling the temperature in both of the temperature zones A and B so as to obtain the optimum yield for acrylic acid. The results are shown in Table 8.

Table 8

| Time elapsed | Reaction temperature (°C.) A | B | S.V. to preceeding catalyst (hr$^{-1}$) | G.C. (mol %) | Acrylic acid single pass yield (mol %) |
|---|---|---|---|---|---|
| Initial | 320 | 255 | 1,350 | 7 | 86.5 |
| 3 month | 320 | 260 | 1,350 | 7 | 86.9 |
| 6 month | 320 | 266 | 1,350 | 7 | 87.5 |
| 12 month | 320 | 270 | 1,350 | 7 | 88.0 |

What is claimed is:

1. A process for catalytic vapor phase oxidation which comprises using a fixed-bed shell and tube heat exchange type reactor in which a bundle of a multiplicity of tubes filled with at least one type of oxidizing catalyst are disposed in a shell and these tubes are passed through the apertures formed in at least one perforated shield plate to partition the inside of the shell into at least two heat transfer medium feed zones and in such a manner that each of the tubes passing through the perforated shield plate is not in direct contaction with the shield plate but the outer surface of the tube and the inner surface of the aperture are spaced apart by a distance of between 0.2–5 mm, supplying feed gas to the tubes of the reactor, and conducting exothermic catalytic vapor phase oxidation while controlling the temperatures for the heat transfer medium in each of the zones so that the temperature difference between each of the zones can be maintained between 0°–100° C.

2. A process according to claim 1, wherein each of the heat transfer medium feed zones is respectively provided with means for circulating the heat transfer medium.

3. A process according to claim 1, wherein the perforated shield plate is provided by one and the inside of the shell is partitioned into two heat transfer medium feed zones.

4. A process according to claim 1, wherein the distance between the outer surface of the tube and the inner surface of the aperture in the perforated shield plate is between 0.3–1 mm.

5. A process according to claim 1, wherein the temperature difference between the heat transfer medium in each of the zones partitioned by the shield plate is between 0°–80° C.

6. A process according to claim 1, wherein annular fins having an outer diameter of a size capable of covering the gap between the outer surface of the tube and the inner surface of the aperture in the perforated shield plate is secured to the tubes in the vicinity of the shield plate.

7. A process according to claim 6, wherein the annular fins are made flat.

8. A process according to claim 6, wherein the annular fins are provided only on one side of the shield plate.

9. A process according to claim 6, wherein the annular fins are provided alternately on both sides of the shield plate.

10. A process according to claim 6, wherein the annular fins are provided so as to outwardly open toward the gap between the tube and the shield plate.

11. A process according to claim 1, wherein one type of an oxidizing catalyst is filled in the reaction tubes.

12. A process according to claim 1, wherein two types of oxidizing catalysts are filled in the reaction tubes.

13. A process according to claim 12, wherein two types of the oxidizing catalysts are filled in the reaction tubes corresponding to each of the zones partitioned by the shield plate respectively.

* * * * *